US008440438B2

(12) United States Patent
Cheng et al.

(10) Patent No.: US 8,440,438 B2
(45) Date of Patent: May 14, 2013

(54) ELECTROMETHANOGENIC REACTOR AND PROCESSES FOR METHANE PRODUCTION

(75) Inventors: Shaoan Cheng, State College, PA (US); Bruce Logan, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 767 days.

(21) Appl. No.: 12/488,951

(22) Filed: Jun. 22, 2009

(65) Prior Publication Data

US 2009/0317882 A1   Dec. 24, 2009

Related U.S. Application Data

(60) Provisional application No. 61/074,296, filed on Jun. 20, 2008.

(51) Int. Cl.
*C12P 5/02* (2006.01)

(52) U.S. Cl.
USPC .......................................................... 435/167

(58) Field of Classification Search .................. None
See application file for complete search history.

(56) References Cited

U.S. PATENT DOCUMENTS

| | | | |
|---|---|---|---|
| 4,067,801 A | 1/1978 | Ishida et al. | |
| 4,503,154 A | 3/1985 | Paton | |
| 4,735,724 A | 4/1988 | Chynoweth et al. | |
| 5,185,079 A | 2/1993 | Dague | |
| 5,443,706 A * | 8/1995 | Kuroda et al. | 204/242 |
| 5,976,719 A | 11/1999 | Kim et al. | |
| 6,270,649 B1 | 8/2001 | Zeikus et al. | |
| 6,299,774 B1 | 10/2001 | Ainsworth et al. | |
| 6,664,101 B2 | 12/2003 | Wild | |
| 7,250,288 B2 | 7/2007 | Zeikus et al. | |
| 7,491,453 B2 | 2/2009 | Logan et al. | |
| 2006/0011491 A1 * | 1/2006 | Logan et al. | 205/637 |
| 2007/0259217 A1 | 11/2007 | Logan | |

OTHER PUBLICATIONS

W.M. Haynes, ed., CRC Handbook of Chemistry and Physics, 92nd Edition (Internet Version 2012). 2012. CRC Press/Taylor and Francis, Boca Raton, FL. pp. 3-1 through 3-3 and 3-344.*
Nelson, DL et al. Lehninger Principles of Biochemistry, 3rd Edition. New York, NY, Worth Publishers, 2000. p. 88.*
Wu, W et al. Microbial composition and characterization of prevalent methanogens and acetogens isolated from syntrophic methanogenic granules. Appl. Microbiol. Biotechnol. 1992. 38: 282-290.*
Diaz, E et al. Molecular ecology of anaerobic granular sludge grown at different conditions. Water Science and Technology. 2003. 48(6): 57-64.*
Wu, W et al. Metabolic properties and kinetics of methanogenic granules. Appl. Microbiol. Biotechnol. 1993. 39: 804-811.*
Kenealy, W et la. Influence of corrinoid antagonists on methanogen metabolism. Journal of Bacteriology. 1981. 146(1): 133-150.*
Zhao, H et al. Assignment of fatty acid-beta-oxidizing syntrophic bacteria to *Syntrophomonadaceae* fam. nov. on the basis of 16S rRNA sequence analyses. International Journal of Systematic Bacteriology. 1993. 43(2): 278-286.*
Wolin, EA et al. Formation of methane by bacterial extracts. Journal of Biological Chemistry. 1963. 238(8): 2882-2886.*
Bond, et al., Electrode-Reducing Microorganisms That Harvest Energy from Marine Sediments, *Science*, 295: 483-485, 2002.
Bond, et al. Electricity Production by *Geobacter sulfurreducens* Attached to Electrodes, *Applied and Environmental Microbiology*, 69(3):1548-155, 2003.
Rabaey, et al., A microbial fuel cell capable of converting glucose to electricity at high rate and efficiency, *Biotechnology Letters*, 25:1531-1535, 2003.
Kim, et al., A mediator-less microbial fuel cell using a metal reducing bacterium, *Shewanella putrefaciens*, *Enzyme and Microbial Technology*, 30: 145-152, 2002.
Park, et al., A Novel Electrochemically Active and Fe(III)-reducing Bacterium Phylogenetically Related to *Clostridium bulyricum* Isolated from a Microbial Fuel Cell, *Anaerobe*, 7: 297-306, 2001.
Chauduri, et al., Electricity generation by direct oxidation of glucose in mediatorless microbial fuel cells, *Nature Biotechnology*, 21(10): 1229-1232, 2003.
Park, et al., Impact of electrode composition on electricity generation in a single-compartment fuel cell using *Shewanella putrefaciens*, *Applied Microbiology and Biotechnology*, 59: 58-61, 2002.
Kim, et al., Effect of initial carbon sources on the performance of microbial fuel cells containing *Proteus vulgaris*, *Biotechnology and Bioengineering*, 70(1): 109-114, 2000.
Park, et al., Electricity Generation in Microbial Fuel Cells Using Neutral Red as an Electronophore, *Applied and Environmental Microbiology*, 66(4):1292-1297, 2000.
Logan, Electricity-producing bacterial communities in microbial fuel cells, Trends in Microbiology 14(12): 512-518, 2006.
Lovley, et al., Anaerobic Oxidation of Toluene, Phenol, and *p*-Cresol by the Dissimilatory Iron-Reducing Organism, GS-15, Applied and Environmental Microbiology, 56(6): 1858-1864, 1990.
Lovley, et al. Novel Mode of Microbial Energy Metabolism: Organic Carbon Oxidation Coupled to Dissimilatory Reduction of Iron or Manganese, Applied and Environmental Microbiology, 54(6): 1472-1480, 1988.
Chernicharo, Anaerobic Reactors: Biological Wastewater Treatment, vol. 4, Biological Wastewater Treatment Series, IWA Publishing, 2007.
Cheng, S. et al., Direct Biological Conversion of Electrical Current into Methane by Electromethanogenesis, *Environmental Science & Technology*, 43(10): 3953-58, 2009.

(Continued)

*Primary Examiner* — Allison Ford
*Assistant Examiner* — Susan E Fernandez
(74) *Attorney, Agent, or Firm* — Gifford, Krass, Sprinkle, Anderson & Citkowski, P.C.

(57) ABSTRACT

Increasing competition for fossil fuels, and the need to avoid release carbon dioxide from combustion of these fuels requires development of new and sustainable approaches for energy production and carbon capture. Biological processes for producing methane gas and capturing carbon from carbon dioxide are provided according to embodiments of the present invention which include providing an electromethanogenic reactor having an anode, a cathode and a plurality of methanogenic microorganisms disposed on the cathode. Electrons and carbon dioxide are provided to the plurality of methanogenic microorganisms disposed on the cathode. The methanogenic microorganisms reduce the carbon dioxide to produce methane gas, even in the absence of hydrogen and/or organic carbon sources.

10 Claims, 5 Drawing Sheets

OTHER PUBLICATIONS

Park, D. et al., Microbial Utilization of Electrically Reduced Neutral Red as the Sole Electron Donor for Growth and Metabolite Production, *Applied and Environmental Microbiology*, 65(7): 2912-17, Jul. 1999.

Ishii, S. et al., Methanogenesis versus Electrogenesis: Morphological and Phylogenetic Comparisons of Microbial Communities, *Bioscience, Biotechnology, and Biochemistry*, 72(2): 286-94, 2008.

He, Z. et al., Application of Bacterial Biocathodes in Microbial Fuel Cells, *Electroanalysis*, 18(19-20): 2009-15, 2006.

Du, Z. et al., A state of the art review on microbial fuel cells: A promising technology for wastewater treatment and bioenergy, *Biotechnology Advances*, 25: 464-82, 2007.

Rozendal, R. et al., Hydrogen Production with a Microbial Biocathode, *Environmental Science & Technology*, 42: 629-34, 2008.

\* cited by examiner

ELECTROMETHANOGENIC REACTOR AND PROCESSES FOR METHANE PRODUCTION

REFERENCE TO RELATED APPLICATION

This application claims priority to U.S. Provisional Patent Application Ser. No. 61/074,296, filed Jun. 20, 2008, the entire content of which is incorporated herein by reference.

GOVERNMENT SUPPORT

This invention was made with government support under Contract Nos. BES-0401885 and CBET-0730359 awarded by the National Science Foundation. The government has certain rights in the invention.

FIELD OF THE INVENTION

The invention relates generally to methods and systems for fuel production, such as methane production. The invention relates generally to methods and systems for carbon capture.

BACKGROUND OF THE INVENTION

Increasing competition for fossil fuels, and the need to avoid release of carbon dioxide from combustion of these fuels requires that we develop new and sustainable approaches for energy production. Microbial fuel cells (MFCs) provide a new method for renewable electricity production from the degradation of organic matter.

Microbial electrolysis cells (MECs) represent another technology that makes use of electrogenic bacteria for wastewater treatment. In an MEC hydrogen gas can be produced by a process called electrohydrogenesis. Hydrogen gas generation is not spontaneous, however, as the voltage produced by the anode using a substrate such as acetate ($E_{An} \cong -0.2$ V in practice) is insufficient for that needed to evolve hydrogen gas the cathode ($E_{cell} = -0.414$ V, pH=7). By adding a small voltage of >0.2 V, however, MECs can produce hydrogen gas at very high energy efficiencies of 200-400 percent based on electrical energy alone, or 82 percent based on both electrical energy and heat of combustion energies for the substrate.

Despite promising developments, there is a continuing need for methods and systems for sustainable production of fuels and for carbon capture.

SUMMARY OF THE INVENTION

Biological processes for producing methane gas are provided according to embodiments of the present invention which include providing an electromethanogenic reactor having an anode, a cathode and a plurality of methanogenic microorganisms disposed on the cathode. Electrons and carbon dioxide are provided to the plurality of methanogenic microorganisms disposed on the cathode. The methanogenic microorganisms reduce the carbon dioxide to produce methane gas, even in the absence of hydrogen and/or organic carbon sources.

An electrical conductor, also termed a conductive conduit herein, exemplified by wire, is disposed such that the anode and the cathode are in electrical communication in particular embodiments. In particular embodiments, the conductive conduit of the electromethanogenic reactor is in electrical communication with a power source and the power source is active to enhance a potential between the anode and the cathode. For example, a wire is connected to the power source from the anode and from the cathode.

Any power source can be used. Examples of power sources used include, without limitation, grid power, wind-generated power, solar power and biomass. Further examples of a power source suitable for use in an inventive system illustratively include a DC power source and an electrochemical cell such as a battery or capacitor. Combinations of two or more of these or other power sources can be used.

In particular embodiments, electrons are transferred to the anode by exoelectrogenic microorganisms. The electrons are transferred to the methanogenic microorganisms at the cathode, such as by a wire in electrical communication with the anode and cathode.

In a particular embodiment, a power source for an electromethanogenic reactor is an electricity producing microbial fuel cell in electrical connection with the electromethanogenic reactor.

Embodiments of methods of the present invention include increasing methane gas production rate in a biological methanogenic reactor by adding an additional voltage to the cathode having methanogenic microorganisms disposed thereon.

Any electromethanogenic reactor configuration can be used. In particular embodiments, the electromethanogenic reactor is configured as a two-chamber reactor including an anode chamber and a cathode chamber. In further embodiments, a single chamber reactor is used.

Optionally, organic carbon sources are substantially excluded from the cathode chamber or substantially excluded from the electromethanogenic reactor. The methanogenic microorganisms reduce carbon dioxide using electrons introduced into the system and no organic carbon source or hydrogen is required for this methane production. Thus, optionally organic carbon is not introduced into the cathode chamber and/or is not introduced into the electromethanogenic reactor. In a further option, organic carbon sources are substantially excluded from the methanogenic microorganisms such as by substantial exclusion from a cathode chamber and/or substantial exclusion from the electromethanogenic reactor.

Optionally hydrogen is not introduced into the cathode chamber and/or is not introduced into the electromethanogenic reactor. Similarly, hydrogen can optionally be substantially excluded from the methanogenic microorganisms such as by substantial exclusion from a cathode chamber and/or substantial exclusion from the electromethanogenic reactor.

In particular embodiments, metal catalysts can be used in methods of the present invention though, optionally, metal catalysts are substantially excluded from the cathode, cathode chamber and/or reactor. In particular embodiments, corrodible metals can be present in the cathode, cathode chamber and/or reactor thought, optionally, corrodible metals are substantially excluded from the cathode, cathode chamber and/or reactor.

Biological processes for producing methane gas are provided according to embodiments of the present invention which include providing an electromethanogenic reactor containing exoelectrogenic microorganisms and methanogenic microorganisms. The exoelectrogenic microorganisms are disposed in direct or indirect electron transfer communication with the anode such that electrons are transferred to the anode. Optionally, the reactor includes an anode chamber and the exoelectrogenic microorganisms are disposed in the anode chamber in direct or indirect electron transfer communication with the anode such that electrons are transferred to the anode. An electrical conductor, such as a wire, is in electrical communication with the anode and cathode such that electrons are transferred from the anode to the cathode according to embodiments of the present invention. The methanogenic microorganisms are disposed in direct or indirect electron transfer communication with the cathode such that electrons are transferred from the cathode. Optionally, the reactor includes a cathode chamber and the methanogenic microorganisms are disposed in the cathode chamber in direct or indirect electron transfer communication with the cathode such that electrons are transferred from the cathode to the methanogenic microorganisms. In preferred embodiments, the methanogenic microorganisms are disposed on the cathode. An organic material oxidizable by oxidizing activity of the exoelectrogenic microorganisms is provided such that electrons are produced, and transferred to the anode and to the plurality of methanogenic microorganisms disposed in the cathode chamber via the electrical conductor. Carbon dioxide is provided to the plurality of methanogenic microorganisms in addition to the electrons and the methanogenic microorganisms reduce the carbon dioxide to produce methane gas.

Biological processes for producing methane gas are provided according to embodiments of the present invention which include providing an electromethanogenic reactor having an anode chamber, a cathode chamber an anode disposed at least partially in the anode chamber, a cathode disposed at least partially in the cathode chamber, a conductive conduit connecting the anode and the cathode, a plurality of exoelectrogenic microorganisms disposed in the anode chamber, and a plurality of methanogenic microorganisms disposed in the cathode chamber. An organic material oxidizable by oxidizing activity of the exoelectrogenic microorganisms is provided such that electrons are produced, and transferred to the anode and to the plurality of methanogenic microorganisms disposed in the cathode chamber via the conductive conduit. Carbon dioxide is provided to the plurality of methanogenic microorganisms in addition to the electrons and the methanogenic microorganisms reduce the carbon dioxide to produce methane gas.

In particular embodiments, at least a portion of the exoelectrogenic microorganisms disposed in the anode chamber are disposed on the anode, forming a biofilm. In particular embodiments, at least a portion of the methanogenic microorganisms disposed in the cathode chamber are disposed on the cathode, forming a biofilm.

Biological processes for producing methane gas are provided according to embodiments of the present invention which include inserting an anode and a cathode into a methanogenic reactor where the reactor contains methanogenic microorganisms. The anode and the cathode are connected by an electron-conductive conduit. Voltage is applied to generate a potential between the anode and the cathode, increasing delivery of electrons to the methanogens and increasing the efficiency of methane production by the methanogenic reactor. Any power source can be used. For example, in particular embodiments, current produced by electrons transferred to the anode by a plurality of exoelectrogenic bacteria is used as a power source. Additional examples of power sources used include, without limitation, grid power, wind-generated power, solar power and biomass. Further examples of a power source suitable for use in an inventive system illustratively include a DC power source and an electrochemical cell such as a battery or capacitor. Combinations of two or more of these or other power sources can be used.

Electromethanogenic reactors are provided according to embodiments of the present invention which include an anode, a cathode and methanogenic microorganisms. In particular embodiments, the methanogenic microorganisms are disposed on the cathode and/or in a cathode chamber. In some embodiments, an electromethanogenic reactor of the present invention further includes exeoelectrogenic microorganisms.

In particular embodiments, the exeoelectrogenic microorganisms are disposed on the anode and/or in an anode chamber.

In further embodiments, an electromethanogenic reactor according to the present invention includes a power source in electrical communication with the reactor to add a voltage to the cathode.

Optionally, a cathode included in an electromethanogenic reactor according to the present invention has a cathode wall generally enclosing and defining an interior space, the cathode wall having an internal surface adjacent the interior space and an opposed external surface, the cathode wall extending between a first end and a second end and wherein the methanogenic microorganisms are disposed in the interior space.

DETAILED DESCRIPTION OF THE INVENTION

Electromethanogenesis processes of the present invention are provided for direct production of methane using a biocathode containing methanogenic microorganisms, both in electrochemical systems using an abiotic anode and in microbial electrolysis cells (MECs) using a biotic anode. Electromethanogenesis can be used to convert electrical current produced from any energy source, including renewable energy sources such as wind, solar, or biomass, into a biofuel (methane) as well as serving as a method for the capture of carbon dioxide.

In specific embodiments, the invention relates to methods for methane production using methanogenic microorganisms to capture carbon and form methane gas from electrons, protons and $CO_2$.

Processes for producing methane gas according to embodiments of the present invention include providing an electromethanogenic reactor having an anode, a cathode, a conductive conduit connecting the anode and the cathode, and a plurality of methanogenic microorganisms disposed on the cathode. Electrons and carbon dioxide are provided to the plurality of methanogenic microorganisms and the carbon dioxide is used as a carbon source to produce methane gas.

For example, the reaction is:

$$CO_2 + 8H^+ + 8e^- \rightarrow CH_4 + 2H_2O$$

The amount of voltage needed for the process is approximated using thermodynamic calculations. The calculated approximate minimum voltage needed under any particular conditions is easily calculated based on the above equation by those skilled in the art. For example, methane can theoretically be produced with microbes on the cathode directly from carbon dioxide at a voltage of 0.169 V under standard conditions (pH=0, or $H^+$=1 M), which means the reaction is highly favorable using microbes that function at pH=0. The calculated approximate minimum voltage is −0.244 V under more biologically standard conditions of pH 7.

By the above calculation at pH=7, methane can be produced using $CO_2$ (−0.244 V) with a lower energy input requirement than that needed for hydrogen production with acetate (−0.414 V, pH=7). Moreover, methane production here is achieved with the capture of carbon dioxide into methane as a part of this process.

It is appreciated that the voltage that is needed to be applied is generally greater than the calculated minimum due to energy losses in the system, such as electrode over potentials.

In particular embodiments of the present invention, organic carbon sources provide little or no carbon for the production of methane. Thus, optionally organic carbon is not introduced into the cathode chamber and/or is not introduced into the electromethanogenic reactor. In a further option, organic carbon sources are substantially excluded from the methanogenic microorganisms such as by substantial exclusion from a cathode chamber and/or substantial exclusion from the electromethanogenic reactor.

In a further option, organic carbon present in the electromethanogenic reactor can be materials which are not available for metabolism by the methanogenic microorganisms. In particular embodiments, acetate, formate, methanol, acetone, methyl amines, carbon monoxide and/or hydrogen are substantially excluded from the electromethanogenic reactor or from a cathode compartment containing the methanogenic microorganisms since these organisms are known to metabolize these substances as described in Wilkie, A. C., "Biomethane from biomass, biowaste, and biofuels," Chapter 16, pp 195-205, In: Bioenergy, Edited by Judy D. Wall, Caroline S. Harwood and Arnold Demain, ASM Press, Washington D.C.

Optionally hydrogen is not introduced into the cathode chamber and/or is not introduced into the electromethanogenic reactor. Similarly, hydrogen can optionally be substantially excluded from the methanogenic microorganisms such as by substantial exclusion from a cathode chamber and/or substantial exclusion from the electromethanogenic reactor.

The terms "substantial exclusion" and "substantially excluded" referring to particular substances such as organic carbon sources, hydrogen, metal catalysts and metals having high corrosion rates are intended to indicate that such substances are not present in amounts sufficient to significantly contribute to methane production. Thus, the terms "substantial exclusion" and "substantially excluded" referring to such substances does not necessarily indicate total absence of substances such as organic carbon sources, hydrogen, metal catalysts and metals having high corrosion rates in a cathode chamber and/or a electromethanogenic reactor.

The term "organic carbon source" is used to refer to an organic compound which can serve as a metabolic substrate for methanogens. The major energy-yielding metabolic reactions of methanogens utilize organic carbon sources such as acetate; formate; alcohols such as methanol, ethanol or propanol; acetone; methyl amines and dimethyl sulfide, resulting in reduction of carbon dioxide to methane. Carbon dioxide is not considered an "organic carbon source."

Methods of methane production according to embodiments of the present invention are performed in one or more electromethanogenic reactors.

Broadly described, an electromethanogenic reactor includes a reaction chamber in which an anode and cathode are at least partially disposed. The reaction chamber may have one or more compartments, such as an anode compartment and a cathode compartment separated, for instance, by a separator or ion exchange membrane, such as a proton exchange membrane or anion exchange membrane. Alternatively, the reaction chamber may be a single compartment configuration. One or more channels may be included in a reaction chamber for addition and removal of various substances such as carbon dioxide and products such as methane.

In particular embodiments, a power source is in electrical communication with the anode and cathode.

In some embodiments, such as where electrons are generated by exoelectrogenic microorganisms, an electrode assembly including an anode, a cathode and an electrically conductive connector connecting the anode and the cathode is included.

Figure 1:
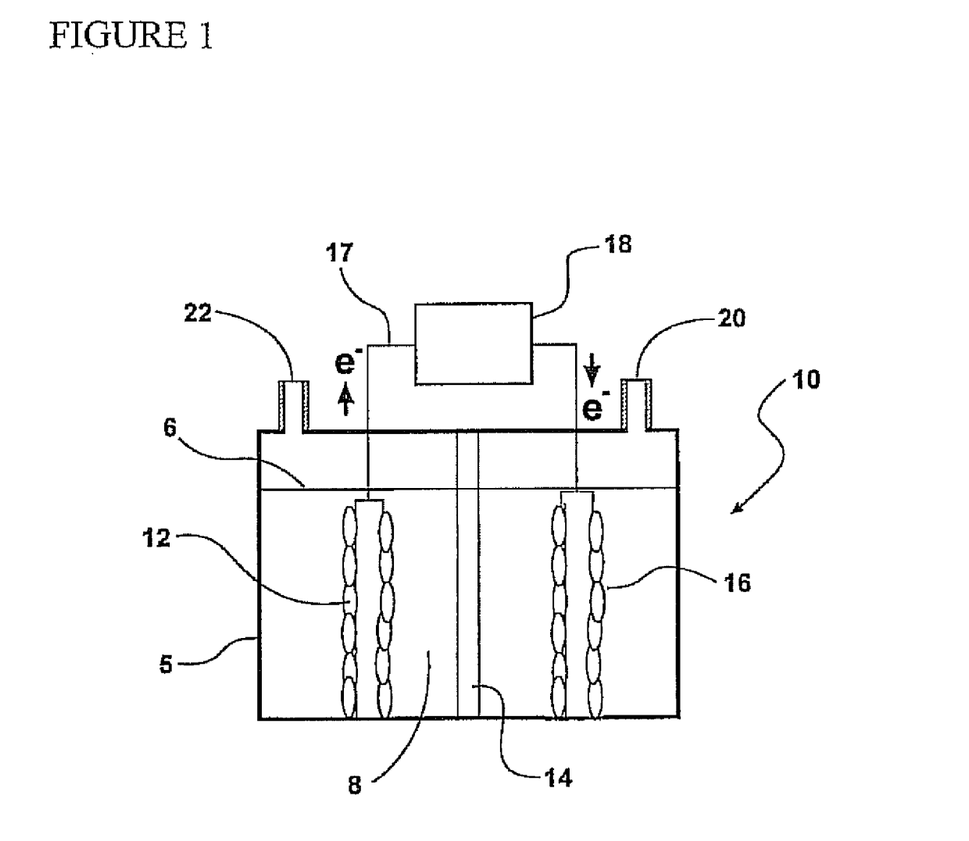
FIG. 1 is a schematic diagram of a methanogenic reactor according to embodiments of the present invention.

FIG. 1 illustrates an embodiment of an electromethanogenic reactor system at 10. In this illustration, a reaction chamber is shown having a wall 5 defining an interior and an exterior of the reaction chamber, and fluid, such as a buffer or an aqueous solution containing oxidizable organic matter, in the interior of the reaction chamber, the fluid level shown at 6. An anode, optionally having exoelectrogenic bacteria disposed thereon, is shown at 12. A cathode having methanogenic microorganisms is shown at 16. A space 8 between the electrodes is further depicted. An optional ion exchange membrane, filter or other separator is shown at 14 positioned between the anode 12 and cathode 16 and defining an anode chamber and a cathode chamber. An electrical connector which is a conduit for electrons 17 is shown along with a connected power source shown at 18. Channels for inflow and/or outflow of materials are shown at 20 and 22.

Electrodes included in an electromethanogenic reactor according to the present invention are electrically conductive. Exemplary conductive electrode materials include, but are not limited to, carbon paper, carbon cloth, carbon felt, carbon wool, carbon foam, graphite, porous graphite, graphite powder, graphite granules, graphite fiber, a conductive polymer, a conductive metal, and combinations of any of these.

Typically, a cathode provides a surface for attachment and growth of methanogens and therefore an included cathode made of material compatible with microbial growth and maintenance. Similarly, an anode provides a surface for attachment and growth of exoelectrogens in particular embodiments and therefore, in such embodiments, an anode is made of material compatible with microbial growth and maintenance. Compatibility of a material with microbial growth and maintenance in an electromethanogenic reactor may be assessed using standard techniques such as assay with a viability marker such as Rhodamine 123, propidium iodide, SYTO 9 and combinations of these or other microbial viability markers.

An anode and cathode may have any of various shapes and dimensions. Electrodes may be positioned in various ways to achieve a desired spacing between the electrodes.

Optionally, an inventive system is provided which includes more than one anode and/or more than one cathode. For example, from 1-100 additional anodes and/or cathodes may be provided. More than 100 additional anodes and/or cathodes can be used in some applications. The number and placement of one or more anodes and/or one or more electrodes may be considered in the context of the particular application. For example, a larger area of cathode surface may be appropriate where a larger volume of carbon dioxide is provided to methanogens and/or where more methane is desired. In a particular embodiment where a large volume of biodegradable substrate is to be metabolized by exoelectrogens in a reactor, a larger area of anodic surface may be provided.

Optionally, a cathode is configured to have an internal space and methanogens are disposed in the internal space. In particular example, an included cathode has a cathode wall generally enclosing and defining an interior space, the cathode wall having an internal surface adjacent the interior space and an opposed external surface, the cathode wall extending between a first end and a second end. Methanogens are disposed in the interior space, such as in contact with the internal surface of the cathode wall in particular embodiments. Optionally, the first and/or second end is closed. The cathode wall can form any of various shapes, such as a tube or hollow slab shape.

Electrodes and reactor configurations include, but are not limited to, those described in U.S. patent application Ser. Nos. 11/180,454 and 11/799,194.

A power source for enhancing the electrical potential between the anode and cathode and providing electrons to the microorganisms is optionally included. While not required for processes of the present invention, use of a power source to add a voltage in an electromethanogenic reactor can increase the rate of desired reactions and increase production of methane.

A power source for enhancing the electrical potential between the anode and cathode can be any of various power sources, including, but not limited to, grid power, solar power sources and wind power sources. Further examples of a power source suitable for use in an inventive system illustratively include a DC power source and an electrochemical cell such as a battery or capacitor.

In particular embodiments, a microbial fuel cell configured to produce electricity is a power source used in the present invention.

Metals having high corrosion rates are not necessary for methanogenic processes according to embodiments of the present invention and may be included or are optionally substantially excluded from the electromethanogenic reactor or from a cathode compartment containing the methanogenic microorganisms. Such metals include highly corrodible iron (Fe(0)), manganese or aluminum, for example.

Autotrophic microorganisms, such as methanogenic microorganisms, capable of using electrons to reduce $CO_2$ are disposed on the cathode of the electromethanogenic reactor.

Microorganisms present on the cathode and/or in a cathode chamber include at least one or more species of methanogenic microbes also called methanogens herein. The terms "methanogens" and "methanogenic microorganisms" as used herein refer to microorganisms characterized by the capacity to perform an eight-electron reduction of carbon dioxide to methane. The major energy-yielding metabolic reactions of methanogens utilize substrates such as acetate; formate; alcohols such as methanol, ethanol or propanol; acetone; methyl amines, dimethyl sulfide, or hydrogen resulting in reduction of carbon dioxide to methane. Methanogenic bacteria are archaebacteria and are obligate anaerobes. Any of various methanogens can be used, illustratively including *Methanobacterium bryantii; Methanobacterium formicum; Methanobrevibacter arboriphilicus; Methanobrevibacter gottschalkii; Methanobrevibacter ruminantium; Methanobrevibacter smithii; Methanocalculus chunghsingensis; Methanococcoides burtonii; Methanococcus aeolicus; Methanococcus deltae; Methanococcus jannaschii; Methanococcus maripaludis; Methanococcus vannielii; Methanocorpusculum labreanum; Methanoculleus bourgensis; Methanogenium olentangyi; Methanogenium bourgense; Methanoculleus marisnigri; Methanofollis liminatans; Methanogenium cariaci; Methanogenium frigidum; Methanogenium organophilum; Methanogenium wolfei; Methanomicrobium mobile; Methanopyrus kandleri; Methanoregula boonei; Methanosaeta concilii; Methanosaeta thermophila; Methanosarcina acetivorans; Methanosarcina barkeri; Methanosarcina mazei; Methanosphaera stadtmanae; Methanospirillum hungatei; Methanothermobacter defluvii; Methanothermobacter thermautotrophicus; Methanothermobacter thermoflexus; Methanothermobacter wolfei; Methanothrix soehngenii; Methanobacterium palustre*; and combinations of any of these and/or other methanogens. Methanogens and conditions for their growth and maintenance are known, as exemplified herein and in M. Dworkin et al., The Prokaryotes, Springer; 3rd edition, 2007.

Methanogens are preferably in contact with a cathode for direct transfer of electrons from the cathode. However, the methanogens may be present elsewhere in the reactor and still function to reduce carbon dioxide to methane using electrons according to embodiments of an inventive process.

Methanogens may be provided as a purified culture, enriched in methanogens, or even enriched in a specified species of microorganism, if desired. Methanogens can be selected or genetically engineered that can increase methane production.

Further, a mixed population of methanogens may be provided, including more than one type of methanogen and optionally including other methanogenic microorganisms. *Methanobacterium palustre* is a preferred microorganism for methane production in systems of the present invention. *Methanobacterium bryantii* is a preferred microorganism for methane production in systems of the present invention.

A gas collection chamber or device is optionally included for capturing the methane gas evolved from the cathode electrode, A methane collection system is optionally included in an inventive electromethanogenic reactor such that the methane generated is collected and may be stored for use, or directed to a point of use, such as to a methane powered device.

For example, a methane collection unit may include one or more methane conduits for directing a flow of methane from the cathode to a storage container or directly to a point of use. For instance, a methane collection system may include a container for collection of methane from the cathode. A collection system may further include a conduit for passage of methane. The conduit and/or container may be in gas flow communication with a channel provided for outflow of methane from an electromethanogenic reactor chamber.

A channel is included defining a passage from the exterior of the reaction chamber to the interior in particular embodiments. More than one channel may be included to allow and/or regulate flow of materials into and out of the reaction chamber. For example, a channel may be included to allow for outflow of methane generated at the cathode. Further, a channel may be included to allow for inflow of carbon dioxide to the methanogens at the cathode.

In a particular embodiment of a continuous flow configuration, a channel may be included to allow flow of a substance into a reaction chamber and a separate channel may be used to allow outflow of a substance from the reaction chamber. More than one channel may be included for use in any inflow or outflow function.

A regulator device, such as a valve, may be included to further regulate flow of materials into and out of the reaction chamber. Further, a cap or seal is optionally used to close a channel. For example, where a fuel cell is operated remotely or as a single use device such that no additional materials are added, a cap or seal is optionally used to close a channel.

A pump may be provided for enhancing flow of liquid or gas into and/or out of a reaction chamber.

In further embodiments, current is generated by exoelectrogenic microorganisms on the anode and/or in an anode chamber, such that electrons are provided to methanogenic microorganisms in the electromethanogenic reactor.

Microorganisms optionally present on the anode and/or in an anode chamber include at least one or more species of exoelectrogenic microorganisms also called exoelectrogens herein. The terms "exoelectrogens" and "exoelectrogenic microorganisms" as used herein refer to microorganisms that transfer electrons to an electrode, either directly or by endogenously produced mediators. In general, exoelectrogens are obligate or facultative anaerobes. The exoelectrogens metabolize a suitable substrate, producing electrons which are transferred to the anode, thereby enhancing the electrical potential between the anode and cathode.

Optionally, bacteria capable of transferring electrons to the anode are included in an electromethanogenic reactor for transfer of electrons to the anode. Bacteria capable of transferring electrons to the anode are exoelectrogens.

Examples of exoelectrogens include bacteria selected from the families Aeromonadaceae, Alteromonadaceae, Clostridiaceae, Comamonadaceae, Desulfuromonaceae, Enterobacteriaceae, Geobacteraceae, Pasturellaceae, and Pseudomonadaceae. These and other examples of microorgansims suitable for use in an inventive system are described in Bond, D. R., et al., Science 295, 483-485, 2002; Bond, D. R. et al., Appl. Environ. Microbiol. 69, 1548-1555, 2003; Rabaey, K., et al., Biotechnol. Lett. 25, 1531-1535, 2003; U.S. Pat. No. 5,976,719; Kim, H. J., et al., Enzyme Microbiol. Tech. 30, 145-152, 2002; Park, H. S., et al., Anaerobe 7, 297-306, 2001; Chauduri, S. K., et al., Nat. Biotechnol., 21:1229-1232, 2003; Park, D. H. et al., Appl. Microbiol. Biotechnol., 59:58-61, 2002; Kim, N. et al., Biotechnol. Bioeng., 70:109-114, 2000; Park, D. H. et al., Appl. Environ. Microbiol., 66, 1292-1297, 2000; Pharn, C. A. et al., Enzyme Microb. Technol., 30: 145-152, 2003; and Logan, B. E., et al, Trends Microbiol., 14(12):512-518.

Exoelectrogens are preferably in contact with an anode for direct transfer of electrons to the anode. However, in the case of exoelectrogens which transfer electrons through a mediator, the exoelectrogens may be present elsewhere in the reactor and still function to produce electrons useful in an inventive process.

Optionally, a mediator of electron transfer is included in a fuel cell. Such mediators are exemplified by ferric oxides, neutral red, anthraquinone-1,6-disulfonic acid (ADQS) and 1,4-napthoquinone (NQ). Mediators are optionally chemically bound to the anode, or the anode modified by various treatments, such as coating, to contain one or more mediators.

Exoelectrogens may be provided as a purified culture, enriched in exoelectrogens, or even enriched in a specified species of microorganism, if desired. Pure culture tests have reported Coulombic efficiencies as high as 98.6% in Bond, D. R. et al., Appl. Environ. Microbiol. 69, 1548-1555, 2003. Thus, the use of selected strains may increase overall electron recovery and hydrogen production, especially where such systems can be used under sterile conditions. Exoelectrogens can be selected or genetically engineered that can increase Coulombic efficiencies and potentials generated at the anode.

Further, a mixed population of exoelectrogens may be provided, including more than one type of exoelectrogenic anaerobe and optionally including other exoelectrogenic microorganisms.

A biodegradable substrate utilized by exoelectrogens such that electrons are produced and transferred to the anode is provided to the exoelectrogens in particular embodiments.

A biodegradable substrate included in a reactor according to embodiments of the present invention is oxidizable by exoelectrogens or biodegradable to produce a material oxidizable by exoelectrogens. In certain embodiments, the biodegradable substrate is excluded from the cathode or cathode compartment, such as by inclusion of a barrier resistant to substrate passage, such as a separator or membrane.

Any of various types of biodegradable organic matter may be used as a biodegradable substrate for microorganisms embodiments of inventive processes, including carbohydrates, amino acids, fats, lipids and proteins, as well as animal, human, municipal, agricultural and industrial wastewaters. Naturally occurring and/or synthetic polymers illustratively including carbohydrates such as chitin and cellulose, and biodegradable plastics such as biodegradable aliphatic polyesters, biodegradable aliphatic-aromatic polyesters, biodegradable polyurethanes and biodegradable polyvinyl alcohols. Specific examples of biodegradable plastics include polyhydroxyalkanoates, polyhydroxybutyrate, polyhydroxyhexanoate, polyhydroxyvalerate, polyglycolic acid, polylactic acid, polycaprolactone, polybutylene succinate, polybutylene succinate adipate, polyethylene succinate, aliphatic-aromatic copolyesters, polyethylene terephthalate, polybutylene adipate/terephthalate and polymethylene adipate/terephthalate.

Organic substrates oxidizable by exoelectrogens are known in the art. Illustrative examples of an organic substrate oxidizable by exoelectrogens include, but are not limited to, monosaccharides, disaccharides, amino acids, straight chain or branched $C_1$-$C_7$ compounds including, but not limited to, alcohols and volatile fatty acids. In addition, organic substrates oxidizable by anodophilic bacteria include aromatic compounds such as toluene, phenol, cresol, benzoic acid, benzyl alcohol and benzaldehyde. Further organic substrates oxidizable by exoelectrogens are described in Lovely, D. R. et al., Applied and Environmental Microbiology 56:1858-1864, 1990. In addition, a provided substrate may be provided in a form which is oxidizable by exoelectrogens or biodegradable to produce an organic substrate oxidizable by exoelectrogens.

Specific examples of organic substrates oxidizable by exoelectrogens include glycerol, glucose, acetate, butyrate, ethanol, cysteine and combinations of any of these or other oxidizable organic substances.

The term "biodegradable" as used herein refers to an organic material decomposed by biological mechanisms illustratively including microbial action, heat and dissolution. Microbial action includes hydrolysis, for example.

Optionally, more than one power source can be used to power an electromethanogenic system of the present invention. For example, where bacteria capable of transferring electrons to the anode are included in an electrogenic reactor for transfer of electrons to the anode, additional voltage can be added from a second source to increase the rate of methane production.

Methods and systems for carbon dioxide capture are provided by the present invention. The efficiency of carbon dioxide capture by electromethanogenesis is high compared to other methods, does not require the use of any metal catalysts, and it is easily accomplished using renewable energy sources. Electrochemical reduction of $CO_2$ with metal catalyzed electrodes have electron capture yields only 10-57 percent, compared to 96 percent using a electromethanogenic method or system according to embodiments of the present invention.

Methods and systems of the present invention are useful in various applications, such as wastewater treatment, renewable energy production, and carbon capture. The energy produced using methods and systems of the present invention can be used in many different ways. For example, many combustion engines can run on natural gas, which mostly consists of methane.

Compression, transport in pipe, and storage of methane involves mature technologies and thus may immediately benefit society as a green and sustainable fuel.

Reaction conditions selected for use in an electromethanogenic reactor can vary depending on the desired application. Reaction temperatures are typically in the range of about 10-40° C. for non-thermophilic microbes, although an electromethanogenic reactor may be used at any temperature in the range of 0 to 100° C. by including microbes suitable for selected temperatures. Where anaerobic microbes are used, reaction conditions are anaerobic.

An electromethanogenic reactor contains a suitable medium or solvent compatible with metabolism of microbes contained therein in particular embodiments of the present invention. A preferred medium is aqueous. Further, the medium or solvent may be adjusted to a be compatible with microbial metabolism, for instance by adjusting pH to be in the range between about pH 3-9, preferably about 5-8.5, inclusive, by adding a buffer to the medium or solvent if necessary, and by adjusting the osmolarity of the medium or solvent by dilution or addition of a osmotically active substance. Ionic strength may be adjusted by dilution or addition of a salt for instance. Further, nutrients, cofactors, vitamins and other such additives may be included to maintain a healthy bacterial population, if desired, see for example examples of such additives described herein and in Lovley and Phillips, Appl. Environ. Microbiol., 54(6): 1472-1480.

Electromethanogenic reactors and electromethanogenic processes described herein can be operated in continuous flow mode or in batch mode according to embodiments of the present invention.

Optionally, methods and systems of the present invention may be used to accelerate wastewater treatment or digestion of other organic material when used in conjunction with known processes. Thus, for example, methods and systems according to embodiments of the present invention include by adding electrodes into a standard anaerobic digester, also known as a methogenic reactor. Such methanogenic reactors are known in the art, such as reactors used for anaerobic microbial wastewater treatment. In such reactors, organic materials, such as wastewater, are converted by anaerobic microbes to by-products, including methane. Those of skill in the art are familiar with standard methogenic reactors suitable for fermenting organic materials using anaerobic microbes. Such reactors and methods of their use are exemplified by those described in U.S. Pat. Nos. 6,299,774; 5,185,079; 4,735,724; 4,503,154; and 4,067,801; and in C.Chernicharo, Anaerobic Reactors: Biological Wastewater Treatment, Volume 4 (Biological Wastewater Treatment Series), IWA Publishing, 2007.

Thus, biological processes for producing methane gas are provided according to embodiments of the present invention which include inserting an anode and a cathode into a methanogenic reactor where the reactor contains methanogenic microorganisms. The anode and the cathode are connected to a power source and voltage is applied to provide electrons to the methanogenic microorganisms, increasing the efficiency of the methanogenic reactor. Any power source can be used. Examples of power sources used include, without limitation, grid power, wind-generated power and solar power. Further examples of a power source suitable for use in an inventive system illustratively include a DC power source and an electrochemical cell such as a battery or capacitor. Combinations of two or more of these or other power sources can be used.

In particular embodiments, elections transferred to the anode by exoelectrogenic microorganisms as described are used as a power source. The anode and the cathode are connected by an electron-conductive conduit such that electrons generated by the exoelectrogenic microorganisms are provided to the methanogenic microorganisms at the cathode.

Embodiments of inventive compositions and methods are illustrated in the following examples. These examples are provided for illustrative purposes and are not considered limitations on the scope of inventive compositions and methods.

EXAMPLE 1

A methanogenic biocathode was developed in a single chamber MEC lacking precious metal catalysts on the electrodes. A single-chamber MEC (SCMEC) (400 mL) was used here that contained a single graphite fiber brush anode (5 cm in diameter and 7 cm long) and several carbon cloth cathodes (14 $cm^2$ each) each coated only with a carbon layer on one side (2.5 $mg/cm^2$, Nafion as binder) and no metal catalyst. Titanium wires were used to connect the electrodes to the circuit. The chamber was sparged with ultra high purity nitrogen gas (99.999%) for 30 min before applying a constant voltage-0.7V (vs Ag/AgCl) to the cathode (working electrode) using a multichannel potentiostat (WMPG100, WonATech, Korea), with the counter and reference poles connected to the anode and reference electrode, respectively.

The SCMEC was inoculated with the solution from an anode chamber of an existing two-chamber MEC reactor, such as described in Cheng, S. et al., Proc. Natl. Acad. Sci. U.S.A., 2007, 104, 18871-18873, containing a Pt-catalyzed cathode, that was producing methane. This reactor was then operated for one month (two cycles in fed-batch mode) with acetate (1 g/L) in a buffered nutrient medium (100 mM phosphate buffer solution; PBS; pH)7) containing (per liter) $NaH_2PO_4.H_2O$, 9.94 g; $Na_2HPO_4.H_2O$, 5.5 g; $NH_4Cl$, 310 mg; KCl, 130 mg; and a minerals solution (12.5 mL) and vitamins solution (5 mL). Concentrations of minerals and vitamins in solutions added to medium were biotin 2.0 mg/l, folic acid 2.0 mg/l, pyridoxine HCl 10.0 mg/l, riboflavin 5.0 mg/l, thiamin 5.0 mg/l, nicotinic acid 5.0 mg/l, pantothenic acid 5.0 mg/l, B-12 0.1 mg/l, p-aminobenzoic acid 5.0 mg/l, thioctic acid 5.0 mg/l, NTA 1.5 g/l, $MgSO_4$ 3.0 g/l, $MnSO4.H_2O$ 0.5 g/l, NaCl 1.0 g/l, $FeSO4.7H_2O$ 0.1 g/l, $CaCl2.2H2O$ 0.1 g/l, $CoCly.6H_2O$ 0.1 g/l, $ZnCl_2$ 0.13 g/l, $CuSO_4.5H_2O$ 0.01 g/l, $AlK(SO_4)_2.12H_2O$ 0.01 g/l, $H_3BO_3$ 0.01 g/l, $Na_2MoO_4$ 0.025 g/l, $NiCl_2.6H_2O$ 0.024 g/l and $Na_2WO_4.2H_2O$ 0.025 g/l.

After one month of operation, this SCMEC produced only methane gas at a rate consistent with current generation. Because this was a single-chamber MEC, however, it was possible that some of the methane produced in this system was from acetoclastic methanogenesis. The anode and one cathode from the reactor were transferred into a two-chamber MEC and acetate was added to the anode chamber and buffer to both chambers. The two-chamber MEC (300 mL each bottle) contained an anion exchange membrane (AMI-7001, Membrane International Inc., U.S.) placed between the anode and cathode chambers (2.9 cmin diameter) (duplicate tests). Each chamber was filled with 250 mL of PBS, acetate (1 g/L)

was added to the anode chamber, and the cathode chamber was initially sparged with $CO_2$.

Voltages reported are with respect to Ag/AgCl reference electrode (+201 mV vs standard hydrogen electrode) that was placed in the chamber to obtain cathode potentials. Experiments were conducted in a constant temperature room (30° C.).

Gas production was quantified according to standard methods using a respirometer and gas chromatography such as described in Logan, B. E. et al, Environ. Sci. Technol., 2008, 42, 8630-8640. Methods for calculating current and energy efficiencies are the same as those described in Cheng, S. et al., Proc. Natl. Acad. Sci. U.S.A., 2007, 104, 18871-18873 for tests with hydrogen gas production, except that here 8 electrons are used for a mole of methane.

At a set voltage of −0.7 to −1V, gas produced in the cathode chamber contained only methane with no detectable hydrogen gas (<1%). No methane was produced using a cathode lacking a biofilm at set potentials as low as −1 V. In contrast, the biofilm cathode produced methane at a set potential of less than −0.7 V but at slower rates.

Figure 3:
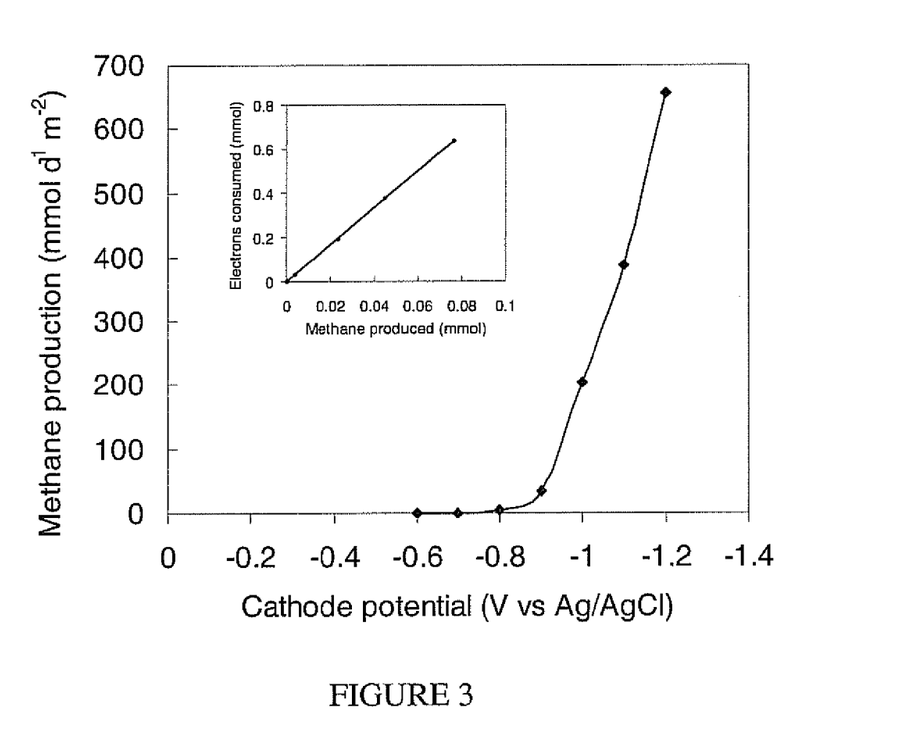
FIG. 3 is a graph illustrating methane production at different set cathode potentials (100 mM PBS, saturated with $CO_2$)

The anode with a biofilm was then removed from the two-chamber MEC and replaced with a plain carbon brush anode (no biofilm) in medium containing only buffer (no acetate). The cathode then initially was sparged with $CO_2$ and sealed. Methane was produced at a rate of 0.9 to 656 mmol-$CH_4 d^{-1} m^{-2}$ (cathode geometric surface area) at set potentials of −0.7 to −1.2 V. FIG. 3 shows methane production at different set cathode potentials (100 mM PBS, saturated with $CO_2$). The rate is calculated over three hours after a two-hour acclimation time. No hydrogen gas was detected in these tests. The lack of acetate in the system ruled out the possibility for acetoclastic methanogenesis.

The process of electromethanogenesis in the absence of acetate was sustained over multiple cycles, each time with the cathode first sparged with $CO_2$, with high recoveries of electrons into methane.

Figure 4:
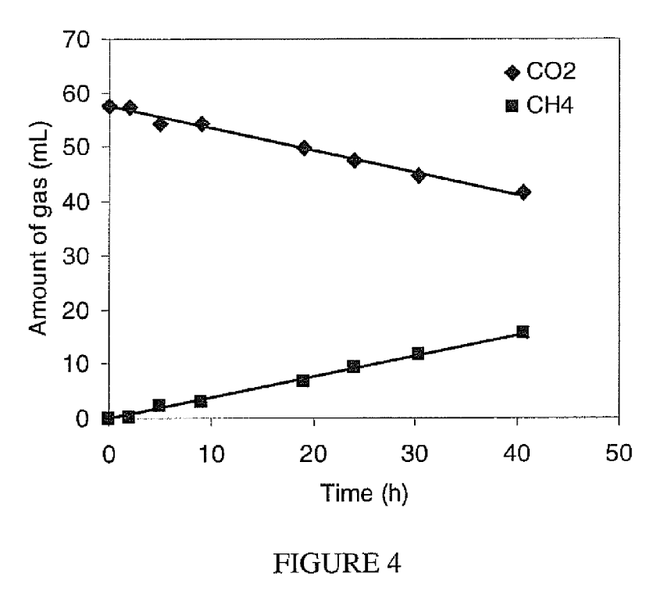
FIG. 4 is a graph illustrating methane formation and loss of carbon dioxide for a set potential of −1 V (100 mM PBS saturated with $CO_2$)

At a set potential of −1.0 V, a two-chamber MEC achieved a sustained methane production rate of ~200 mmol-$CH_4 d^{-1} m^{-2}$ with a $CO_2$ consumption rate of ~210 mmol-$CO_2 d^{-1} m^{-2}$. Based on this rate, 8.33 mol of electrons were required to produce 1 mole of methane, indicating 96 percent current capture into methane. FIG. 4 shows methane formation and loss of carbon dioxide at a set potential of −1.0V (100 mM PBS saturated with $CO_2$). The use of different potentials can be used to vary the rate of gas production.

Using the single-chamber MEC at a set voltage of −1V, an overall energy recovery of 80% was achieved based on electrical energy and the acetate (heat of combustion).

Figure 2:
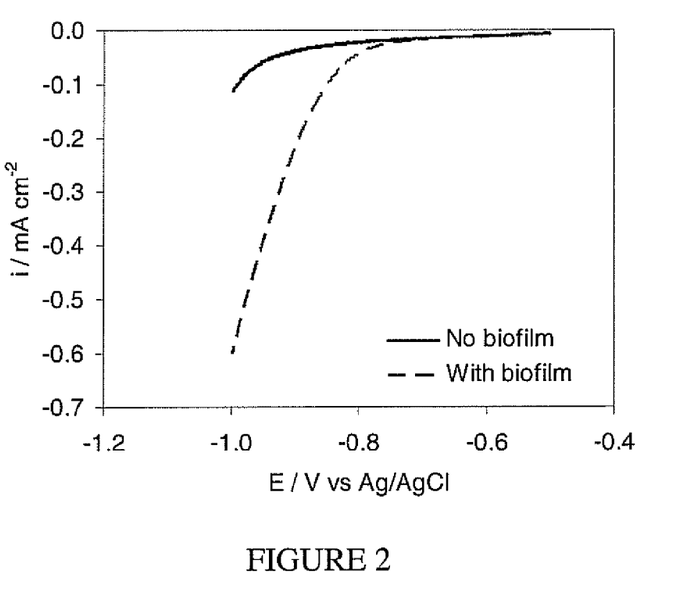
FIG. 2 is a graph illustrating linear sweep voltammograms of cathodes in the presence and absence of a biofilm (1 mV/s using $CO_2$ saturated medium, 100 mM PBS)

Linear sweep voltammetry (LSV) is used to determine the current densities the absence and presence of the biofilm on the cathode. LSV using a plain carbon electrode (no Pt) and was conducted in the potential range from −0.5 to −1.0 V at a low scan rate of 1 mV/s. LSV shows that there was little current compared to that obtained with a biocathode, until potentials were more negative than −0.95 V, compared to −0.65 V with the biocathode. FIG. 2 shows linear sweep voltammograms of cathodes in the presence and absence of a biofilm (1.0 mV/s using $CO_2$ saturated medium, 100 mM PBS).

Hydrogen evolution rates from the cathode could not support hydrogenotrophic methanogenesis. Linear sweep voltammetry showed that there was little electrochemical activity until potentials were less than −1.0 V. Even if hydrogen was produced at the cathode at these potentials, the current generated would be insufficient to support sufficient hydrogen evolution to sustain the gas production of methane from the biocathode.

Further evidence to support methane production without the need for hydrogen evolution was obtained by chemically removing hydrogen gas and examining current generation using LSV. When the cathode was coated with a hydrogen scavenger (1,4-diphenyl-butadiyne), current densities were not increased compared to those obtained with an uncoated electrode.

Figure 5A:
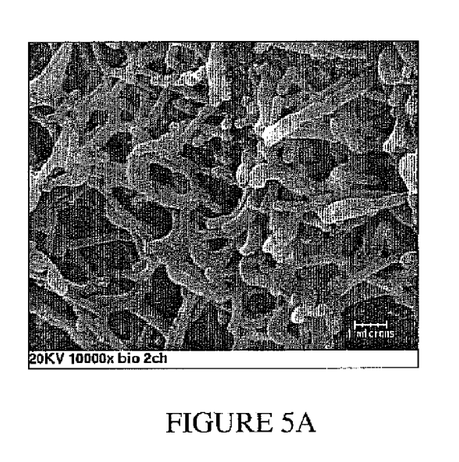
FIG. 5A is a cathode biofilm examined by Scanning Electron Microscopy (SEM) of cells on the carbon cloth.
Figure 5B:
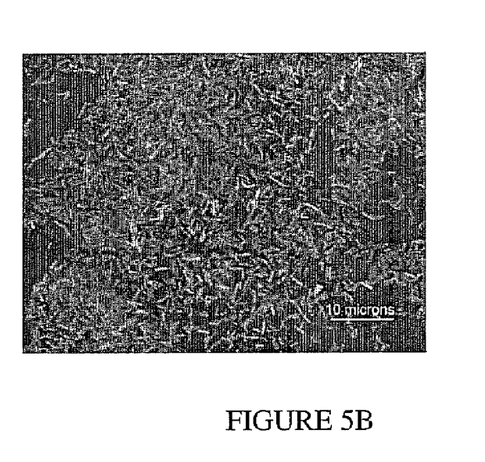
FIG. 5B is a cathode biofilm examined by fluorescence microscopy of extracted cells using the *Methanobacterium*-specific probe MB1174-Alexa Fluor 488.

Examination of the biofilm by SEM showed that it was composed of cells with a homogeneous morphology and a loose structure (FIG. 5A). Based on phylotypes with a 99 percent minimum similarity threshold, community analysis indicated the dominant populations were composed of several phylotypes of the Archaea domain consisting of *Methanobacterium palustre, Methanoregula boonei*, and *Methanospirillum hungatei*. There were also several phlyotopes of the Bacteria domain also present in the biofilm which were all gram-positive bacteria, consisting of *Sedimentibacter hongkongensis, Clostridium sticklandii, Clostridium aminobutyricum* and an uncultured bacterium with was most closely related to *Caloramator coolhaasii*. Staining the biofilm using FISH showed that *Methanobacterium* accounted for 86.7±2.4 percent (n=5) of the total cells (FIG. 5B). Based on the dominance of the DGGE bands by one species and FISH results, the main microorganism responsible for methane generation was *Methanobacterium palustre* in this system.

Analysis of the Biofilm.

Two pairs of universal primers of domains Archaea and Bacteria were used for PCR amplification of 16S rRNA gene: Arc341F, 5' CCTAYGGGGYGCASCAGGCG-3' (SEQ ID No. 1) or Bac968F, 5'-AACGCGAAGAACCTTAC-3' (SEQ ID No. 2) which were attached a GC clamp (CGCCCGC-CGCGCCCCGCGCCCGTCCCGCCGCCCCGCCCG) (SEQ ID No. 3) at the 5'-terminus, and Arc915R: 5'-GT-GCTCCCCCGCCAATTCCT-3' (SEQ ID No. 4) or Bac1401R, 5'-CGGTGTGTACAAGACCC-3' (SEQ ID No. 5). Denaturing gradient gel electrophoresis (DGGE), sequencing, and phylogenetic analyses were carried out as described in Xing, D. et al., Appl. Environ. Microbiol., 2008, 74, 1232-1239. Briefly described, DGGE is performed with a DCode universal mutation detection system (Bio-Rad Laboratories, Hercules, Calif.). A double-gradient gel is used for analyzing amplified 16S rRNA gene products. A second gradient of 6 to 12% polyacrylamide (acrylamide/bisacrylamide ratio, 37.5:1) together with a 30 to 60% denaturing gradient is superimposed as described in Cremonesi, L. et al., 1997, BioTechniques 22:326-330 and Muyzer, G., 1999, Curr. Opin. Microbiol. 2:317-322. One hundred percent denaturation corresponds to 7 M urea and 40% (vol/vol) deionized formamide. A gradient gel is cast with a gradient delivery system (model 475; Bio-Rad). Approximately 1 µg of PCR or RT-PCR products per lane is loaded onto DGGE gels.

Electrophoresis is run under suitable conditions in 1× Tris-acetate-EDTA buffer maintained at 60° C. The gels are silver stained according to the method of Bassam, B. J. et al., 1991. Anal. Biochem. 196:80-83. Prominent DGGE bands are selected and excised for nucleotide sequencing. The gel is crushed in 50 µl TE buffer (10 mM Tris-HCl, 1 mM EDTA [pH 8.0]), and the mixture is allowed to equilibrate overnight at 4° C. After the slurry is centrifuged at 5,000×g for 1 min, 1 µl of buffer containing DNA is used as the template for a PCR performed under the conditions described above for biofilm samples, except that the forward primer lacks the GC clamp. The PCR products are purified with a Gel Recovery purification kit and cloned into *Escherichia coli* JM109 using the pGEM-T plasmid vector system (Promega, Madison, Wis.) in accordance with the manufacturer's instructions. Ten clones from each band are randomly chosen for reamplification with the GC clamp. Five microliters of reamplification product from each clone is subjected to DGGE analysis as described above for biofilm samples in order to check the purity and to confirm the melting behavior of the band recovered. If the bands from the clones are identical with the DGGE parents' bands, these clones from the same band are sequenced to estimate the numbers of particular types of sequences comigrating on the DGGE band.

PCR or RT-PCR products are purified, ligated into vector pCR2.1 using a TOPO TA cloning kit (Invitrogen, Carlsbad, Calif.), and cloned into chemically competent One Shot *Escherichia coli* cells, provided with the cloning kit, according to the manufacturer's instructions. From these transformants, clone libraries of the selected genes from the biofilm are constructed. The cloned PCR fragments are sequenced using standard sequencing techniques.

The 16S rRNA sequences are analyzed against the Gen-Bank database and Ribosomal Database Project II (RDP II; http://rdp.cme.msu.edu). All sequences are examined for chimerism using the CHECK_CHIMERA program at RDP II and BELLEROPHON (http://foo.maths.uq.edu.au/huber/bellerophon.pl) as described in Huber, T. et al., 2004, Bioinformatics 20:2317-2319. Neighbor-joining phylogenetic trees of 16S rRNA are constructed with the molecular evolutionary genetics analysis package (MEGA, version 3.1) and the Jukes-Cantor algorithm as described in Kumar, S. et al., 2001, 17:1244-1245. A bootstrap analysis with 1,000 replicates is carried out to check the robustness of the tree.

The 16S rRNA gene sequences from this study have been deposited in the GenBank database under accession numbers EU812208-EU812220. A genus-specific probe for *Methanobacterium*, MB 1174, 5' TACCGTCGTCCACTCCTTC-CTC-3' (SEQ ID No. 6), was synthesized and labeled with Alexa Fluor 488 (Invitrogen, Molecular Probes). The cathodes were rinsed twice by phosphate-buffered saline (PBS; 0.13 MNaCl and 10 mMNa2HPO4 at pH 7.2), and then cells were extracted using a sterile razor and fixed with 4% paraformaldehyde for 30 min. Hybridizations were performed at 46° C. for 10 h with buffer (0.9 M NaCl, 20 mM Tris-HCl [pH 7.2], 0.01 sodium dodecyl sulfate and 35% formamide) containing 5 ng probe per microliter and then washed with buffer (30 min at 48° C.). FISH was performed on an Olympus FV 1000 confocal laser scanning microscope. The percent of *Methanobacterium* in the total cells was calculated by comparison between fluorescent and differential interference contrast (DIC) pictures by the ImageJ (http://rsb.info.nih.gov/ij/).

Pure Culture Tests.

*Methanobacterium palustre* was purchased from the American Type Culture Collection (ATCC BAA-1077). The strain was cultured anaerobically [$H_2$-$CO_2$ (80:20, vol/vol)] in the ATCC specified medium using 125 mL serum bottles with thick rubber stoppers. Prior to inoculation into MECs, 75 mL of culture solution after incubation was centrifuged and resuspended in sterile phosphate buffered nutrient medium lacking electron donor and acceptor. This cell suspension was inoculated into the anaerobic cathodic chamber and immediately sparged with CO2.

Figure 6A:
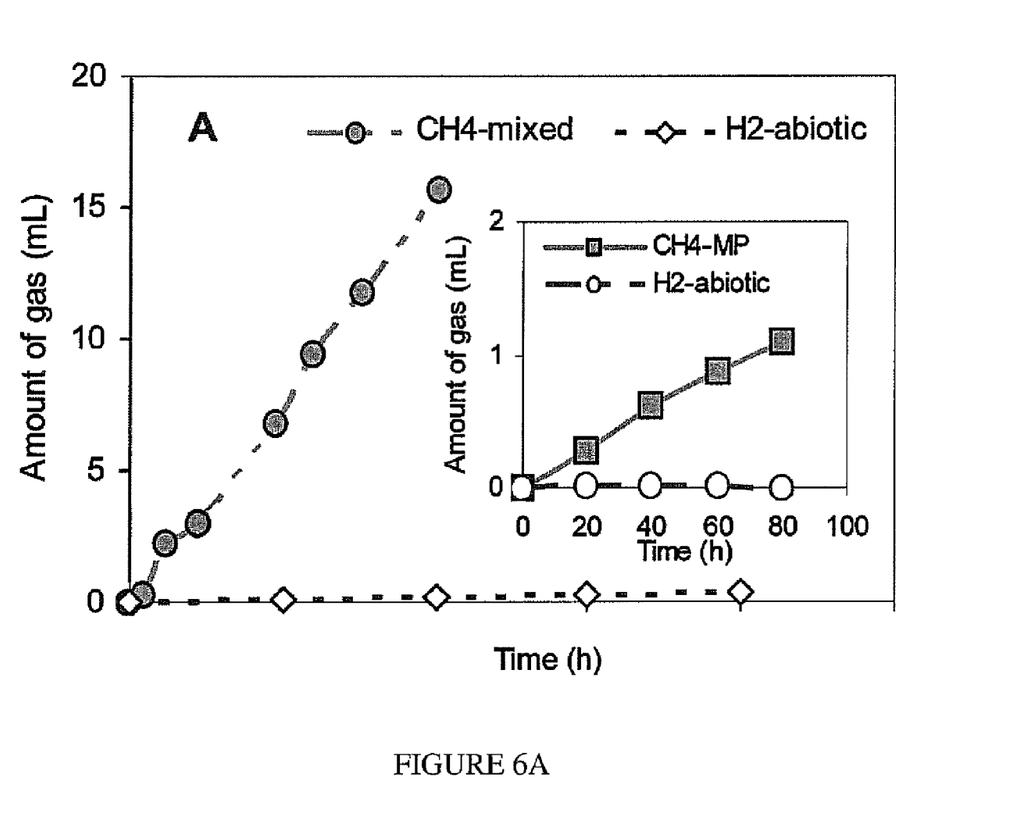
FIG. 6A is a graph showing methane gas production from a mixed culture biofilm (CH4-mixed) compared to methane gas production in absence of a biofilm (H2-abiotic)

FIG. 6A is a graph showing methane gas production from a mixed culture biofilm (CH4-mixed) compared to methane gas production in absence of a biofilm (H2-abiotic). No hydrogen gas was detected in mixed biofilm tests.

There was some hydrogen gas evolution from an abiotic cathode, but it was too low (FIG. 6A) to account for observed rates of methane production by the biocathode. Thus, only in the presence of the biofilm was current generation enhanced. This enhancement could not occur without microorganisms catalyzing the release of these electrons. Stirring the solution did not substantially affect current generation, demonstrating that current generation was not substantially affected by mass transfer. Thus, the increase in current generation provides electrochemical evidence of direct electron transfer from the cathode to the biofilm. The inset of FIG. 6A shows that methane gas is lower using a biocathode with a pure culture of *M. palustre* (CH4-Mp) but this gas production is still larger than that of an abiotic cathode (H2-abiotic). A trace level of hydrogen gas (0.01%) was detected in tests with *M. palustre*.

Figure 6B:
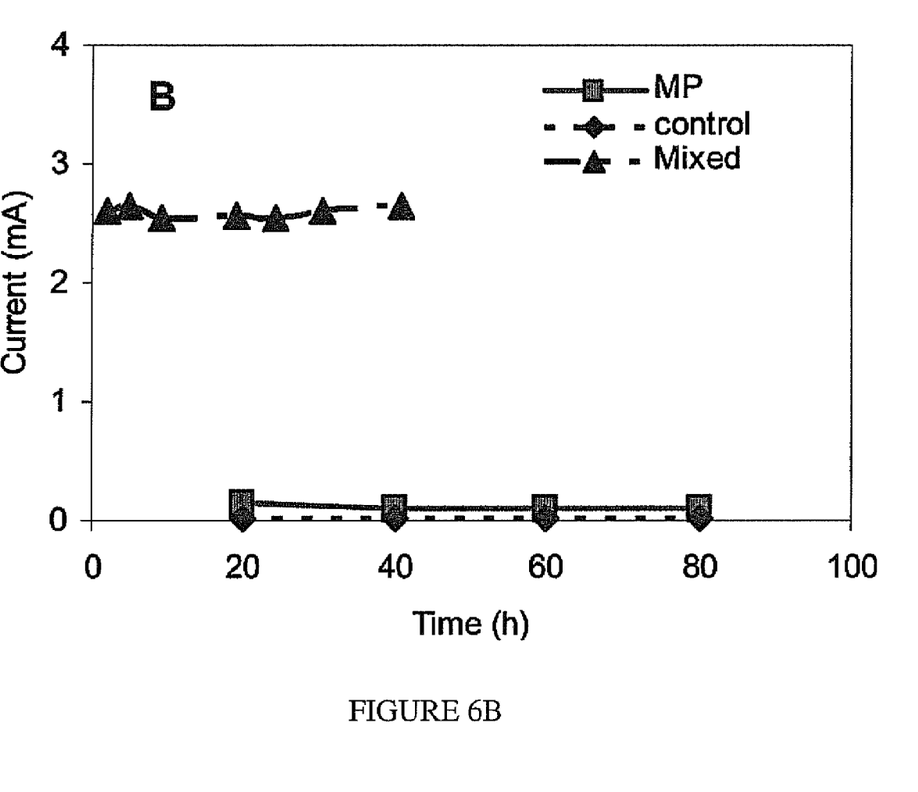
FIG. 6B is a graph showing current densities measured using a mixed culture biofilm, *M. palustre*, or in the absence of microorganisms (applied potential of −1.0V).

In order to further examine the effect of microorganisms on current generation, current and methane generation were examined in pure-culture MEC tests using the type strain. FIG. 6B is a graph showing current densities measured using a mixed culture biofilm, *M. palustre*, or in the absence of microorganisms (applied potential of −1.0V).

Methane was produced using a biocathode of a pure culture of *M. palustre* ATCC BAA-1077. However, the current density and methane production were much lower than those with the mixed culture biofilm (FIG. 6B). Even under these lower current conditions, however, methane was still produced by *M. palustre* at a rate (14×) greater than that expected from the hydrogen evolved in the absence of microorganisms.

References

Call, D. and Logan, B. E. (2008) Hydrogen production in a single chamber microbial electrolysis cell (MEC) lacking a membrane. Environ. Sci. Technol. 42(9), 3401-3406.

Cheng, S. and Logan, B. E. (2007) Sustainable and efficient biohydrogen production via electrohydrogenesis. Proc. Natl. Acad. Sci. USA 104(47), 18871-18873.

Clauwaert, P., Toledo, R., Ha, D.v.d., Crab, R., Verstraete, W., Hu, H., Udert, K. M. and Rabaey, K. (2008) Combining biocatalyzed electrolysis with anaerobic digestion. Wat. Sci. Technol. 57(4), 575-579.

Daniels, L., Belay, N., Rajogopal, B. S. and Weimer, P. J. (1987) Bacterial methanogenesis and growth from $CO_2$ with elemental iron as the sole source of electrons. Science 237, 509-511.

Gregory, K. B., Bond, D. R. and Lovley, D. R. (2004) Graphite electrodes as electron donors for anaerobic repiration. Environ. Microbiol. 6, 596-604.

Liu, H., Grot, S. and Logan, B. E. (2005) Electrochemically assisted microbial production of hydrogen from acetate. Environ. Sci. Technol. 39(11), 4317-4320.

Logan, B. E. (2008) Microbial fuel cells, John Wiley & Sons, Inc.

Logan, B. E. and Regan, J. M. (2006) Electricity-producing bacterial communities in microbial fuel cells. Trends Microbiol. 14(12), 512-518.

Rozendal, R. A., Jeremiasse, A. W., Hamelers, H. V. M. and Buisman, C. J. N. (2008) Hydrogen production with a microbial biocathode. Environ. Sci. Technol. 42(2), 629-634.

Tartakovsky, B., Manuel, M.-F, Neburchilov, V., Wang, H. and Guiot, S. R. (2008) Biocatalyzed hydrogen production in a continuous flow microbial fuel cell with a gas phase cathode. J. Power Sour., doi:10.1016/j.jpowsour.2008.1003.1062.

Any patents or publications mentioned in this specification are incorporated herein by reference to the same extent as if each individual publication is specifically and individually indicated to be incorporated by reference. U.S. Provisional Patent Application Ser. No. 61/074,296, filed Jun. 20, 2008, is incorporated herein by reference in its entirety.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A biological process for producing methane gas comprising:
   providing an electromethanogenic reactor having an anode, a cathode, and a plurality of methanogenic microorganisms disposed on the cathode, the plurality of methanogenic microorganisms comprising at least two phylotypes of methanogenic microorganisms of the Archaea domain;
   providing electrons to the plurality of methanogenic microorganisms disposed on the cathode, wherein no mediator of electron transfer is present in the electromethanogenic reactor; and
   providing carbon dioxide to the plurality of methanogenic microorganisms and substantially excluding hydrogen from the electromethanogenic reactor such that hydrogen gas does not contribute to methane production by the methanogenic microorganisms, whereby the methanogenic microorganisms reduce the carbon dioxide in the absence of hydrogen gas to produce methane gas.

2. The process of claim 1, wherein a power source is in electrical communication with the reactor to enhance a potential between the anode and the cathode.

3. The process of claim 1, wherein electrons provided to the plurality of methanogenic microorganisms comprises electrons transferred to the anode by a plurality of exoelectrogenic bacteria.

4. The process of claim 2, wherein the power source is selected from the group consisting of: wind-generated power, solar power, a microbial fuel cell, a DC power source, an electrochemical cell, and a combination of two or more thereof.

5. The process of claim 1, further comprising increasing methane gas production rate by adding an additional voltage to the cathode.

6. The process of claim 1 wherein the electromethanogenic reactor comprises an anode chamber and a cathode chamber.

7. The process of claim 6 wherein no organic carbon source is added to the cathode chamber.

8. The process of claim 6 wherein no hydrogen is added to the cathode chamber.

9. The process of claim 1, wherein substantially no organic carbon source is available to the plurality of methanogenic microorganisms.

10. The process of claim 1, wherein metal catalysts are substantially excluded from the cathode.

* * * * *

UNITED STATES PATENT AND TRADEMARK OFFICE
CERTIFICATE OF CORRECTION

| | |
|---|---|
| PATENT NO. | : 8,440,438 B2 |
| APPLICATION NO. | : 12/488951 |
| DATED | : May 14, 2013 |
| INVENTOR(S) | : Shaoan Cheng et al. |

Page 1 of 1

It is certified that error appears in the above-identified patent and that said Letters Patent is hereby corrected as shown below:

In the Specification:

At column 8, line number 40, Delete "electrode, A", Insert -- electrode. A --

At column 9, line number 44, Delete "et al,", Insert -- et al., --

At column 12, line number 8, Delete "elections", Insert -- electrons --

At column 15, line number 33, Delete "earned", Insert -- carried --

Signed and Sealed this
Sixth Day of January, 2015

Michelle K. Lee
*Deputy Director of the United States Patent and Trademark Office*